United States Patent [19]

Wolff et al.

[11] 4,313,679
[45] Feb. 2, 1982

[54] TEST SAMPLE SUPPORT ASSEMBLY

[75] Inventors: Ernest G. Wolff, Rolling Hills Estates; Steven A. Eselun, Long Beach, both of Calif.

[73] Assignee: The United States of America as represented by the Secretary of the Air Force, Washington, D.C.

[21] Appl. No.: 98,429

[22] Filed: Nov. 29, 1979

[51] Int. Cl.³ .................... G01N 21/01; G01B 11/02; G01N 25/16
[52] U.S. Cl. ........................................ 356/244; 73/16; 219/10.67; 356/358
[58] Field of Search ................ 356/244, 345, 357–358, 356/360, 35.5, 32; 350/253; 333/229, 234; 331/94.5 T, 94.5 S, 94.5 C; 357/80; 219/10.67; 73/766, 16

[56] References Cited

U.S. PATENT DOCUMENTS 3,619,463 11/1971 Budlin et al. ........................... 73/16
3,930,730 1/1976 Laurens et al. .
3,938,889 2/1976 McKinnis .

FOREIGN PATENT DOCUMENTS 2502086 7/1976 Fed. Rep. of Germany ...... 356/358

OTHER PUBLICATIONS

Wolff et al., "Absolute Length Changes by Remote Interferometry", Samso-TR-75-284, 12-10-75.
Bloss, R. L., "An Extensometer for Use as a Laboratory Standard at Temperatures to 1500° C.", ISA Trans., vol. 10, 1971, pp. 242–249.
Wolff et al., "Double Michelson Interferometer for Contactless Length Change Measurements", Samso–TR-78-136, 11-6-78.

Primary Examiner—William H. Punter
Attorney, Agent, or Firm—Donald J. Singer; Jacob N. Erlich

[57] ABSTRACT

A test sample support assembly having its greatest utility in a length measuring device in a temperature controlled environment. The sample support assembly has a main support, a pair of insulating members and a sample support. In one embodiment of this invention the sample support is made of a substantially distortion-free material thereby precisely positioning the sample within the temperature controlled environment. In the other embodiment of this invention the sample support acts as the temperature controlling element. The sample support is adjustably mounted with respect to the main support. This adjustable feature permits corrective movement of the sample support to take place in order to compensate for the undesirable movement of the sample support.

8 Claims, 3 Drawing Figures

TEST SAMPLE SUPPORT ASSEMBLY

STATEMENT OF GOVERNMENT INTEREST

The invention described herein may be manufactured and used by or for the Government for governmental purposes without the payment of any royalty thereon.

BACKGROUND OF THE INVENTION

This invention relates generally to contactless length measurement devices, and, more particularly to a test sample support assembly for use with such contactless length measurement devices.

Dimensionally stable materials find great utility as aerospace components such as microwave filters and waveguides, antenna structures and supports, laser or optic platforms, instrument parts, solar cell connectors and mounts, cryogenic piping and the like. In addition, low expansion materials are required for guidance systems, space telescopes, and most communications, navigation, scientific and surveillance satllites.

Unfortunately, in spite of "near-zero" expansivities of such dimensionally stable materials as Invar, $TiO_2$-$SiO_2$ glasses, and multi-ply graphite-epoxy composites, no materials yet exist that exhibit thermal strain of less than $6 \times 10^{-5}$ over the aerospace working range, $0° \pm 200°$ C. Consequently, a high-precision dilatometer is needed to measure dimensional changes over a wide temperature range. Ideally, effects that are due to residual stress relief, moisture desorption, and thermal cycling, as well as expansivity, should be measurable for both aerospace components and specially fabricated test samples.

It is well recognized that the utilization of remote or "contactless" measurement devices are the most effective in overcoming the above mentioned problems. This is so, since the thermal expansion coefficient, by definition, must be characterized at a constant pressure:

$$\beta = V^{-1}(dV/dT)_p \quad \text{or} \quad \alpha = (d\epsilon/dT)_p$$

Since expansivity varies with applied stress and many materials lack a true elastic limit, mechanical constraints should be avoided. Contacts may cause microcreep and surface contamination or damage. The position, stability, and thermal properties of contacts affect measurements, especially of real time data, because of thermal lag. A contactless measurement technique permits arbitrary sample size or shape, thereby minimizing fabrication effects on a sample or component. In addition, contactless measurements reduce temperature range restrictions and equilibration requirements and permit simultaneous thermal diffusivity measurements.

Contactless length measurement techniques have been performed by a variety of apparatus. Stationary light beams, from lasers or autocollimators, may be reflected off sample ends. The Fototonic fiber optics approach is, in principal, similar. Scanning techniques include single laser systems, multiple lasers or multiple sensors. Photographic techniques include Moire, speckle, and holographic interferometry. The most accurate approach, however, has been accomplished by Michelson interferometry.

The use of such interferometric techniques for length measurements results in the elimination of dependence on a reference material. The laser frequency can be readily known and stabilized, through use of the Lamb dip, to one part in $10^9$ in 500 hours. When all the optics are placed in a test (vacuum) chamber possible errors from variable beam speeds, window effects, or operators are minimized.

With the basic Michelson interferometer measurement determining device, one arm of the interferometer includes both ends of the test sample, which unfortunately, results in a large optical path length difference (OPLD) between the two beams required to recombine in order to form the necessary fringe pattern. It has been determined that these several possible sources of error are inherent in such an approach. Because the optical path length to the sample was substantially greater (70 times) than that to the reference mirror, errors arose as a result of difference in pressure or temperature of the residual gas in the two optical path lengths (OPLs).

This situation has been overcome by the utilization of the Two Channel Michelson Interferometer. Unfortunately, since all the optics utilized even in the Two Channel Michelson Interferometer used in the sample optical path length were held on the same support plate, any temperature changes in any part of this plate would change the sample optical path length. Consequently, the interferometer would confuse this optical path length change with a sample length change.

In principle, such an error could be avoided by a zero coefficient of thermal expansion support plate. This would be approximated by ultra-low-expansion (ULE) glass near room temperature (CTE $\sim 0 \pm 0.03 \times 10^{-6}$ degrees C.$^{-1}$). A sufficiently large and stiff plate, however, is extremely expensive (stiffness provides immunity from vacuum chamber distortions on pump down or ambient temperature fluctuations). The error might also be avoided by the use of a water-cooled copper base plate attached to a thermostatically controlled bath. Undesirable vibrations could result, however, because the optics would have to be attached rigidly to the plate.

It is therefore clearly apparent that a need arises for a support assembly which is capable of supporting a test sample or the like within a length measuring device and yet remain unaffected by the surrounding temperatures. In so doing sample optical path length would not be altered due to the surrounding temperatures.

SUMMARY OF THE INVENTION

The test sample support assembly of this invention overcomes the problems set forth in detail hereinabove by providing a support assembly which remains virtually unaffected by the surrounding temperatures. In addition, the test sample support assembly of this invention, although finding its greatest utility within a sample length measuring device, such as the Two Channel Michelson Interferometer, may also, if desired, be utilized in any instance wherein surrounding environmental conditions would cause distortion of the support.

The test sample support assembly of this invention relies upon a main support which is made of any suitable material having an ultra-low expansion property to mount a sample support thereon. As a result, this arrangement minimizes movement of the optical apparatus secured thereto. In addition to this property of the main support, it is also essential to further insulate this main support from the temperature distribution of the surrounding environment. This is accomplished by the utilization of a high thermal conductive insulating member juxtaposed the main support. The high thermal conductivity of this insulation member substantially eliminates temperature gradients within the main support. Located juxtaposed the first insulation material is another insulating block of material.

In one embodiment of this invention, the actual sample support is made of a substantially distortion-free material and is mounted upon the main support. The sample support protrudes through openings within the two insulating members. In this manner the sample support precisely positions the sample within either a heated or cooled environment in which the length measurements can be taken.

In the other embodiment of this invention, the sample support is made of a highly conductive material having a hollow interior through which a coolant may flow. This sample support is positioned relative to the main support by means of a pair of rods. The rods have attached thereto resistant heaters which enable the rods to either expand or contract in a predetermined manner. This expansion or contraction allows for adjustable movement of the sample support to take place in order to compensate for the undesirable movement of the sample support.

It is therefore an object of this invention to provide a test sample support assembly which is virtually unaffected by surrounding temperatures.

It is another object of this invention to provide a test sample support assembly which incorporates therein an adjustable member capable of providing compensation for any movement of the support which may take place.

It is a further object of this invention to provide a test sample support assembly which is economical to produce and which utilizes conventional, currently available components that lend themselves to standard mass producing manufacturing techniques.

For a better understanding of the present invention, together with other and further objects thereof, reference is made to the following description taken in conjunction with the accompanying drawing and its scope will be pointed out in the appended claims.

DETAILED DESCRIPTION OF THE DRAWING

DETAILED DESCRIPTION OF THE PREFERRED EMBODIMENTS

Figure 1:
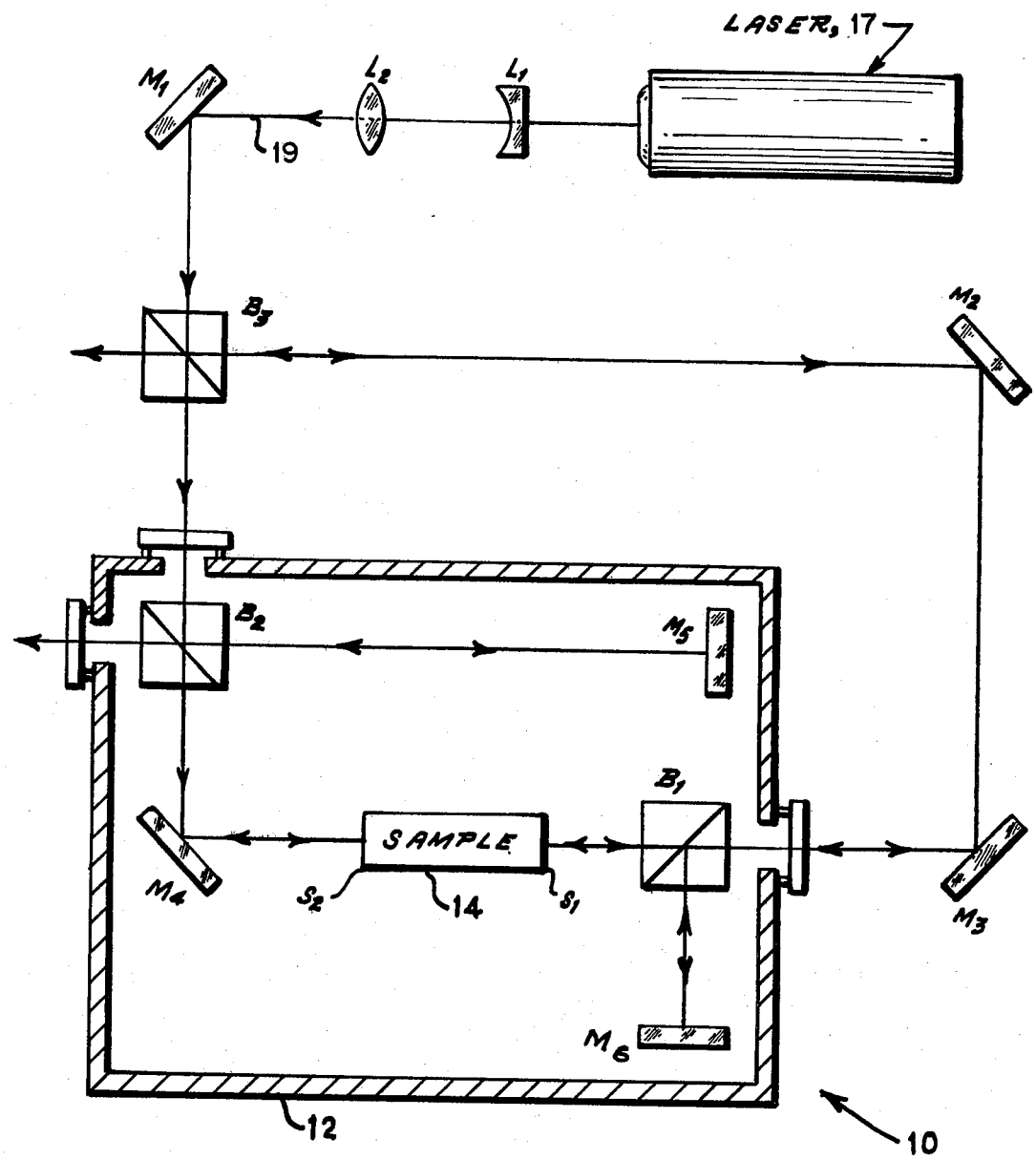
FIG. 1 is a schematic representation of the Two Channel Michelson Interferometer in which the test sample support assembly of this invention can be utilized.

Reference is now made to FIG. 1 of the drawing which schematically illustrates a standard length measuring apparatus, such as a Two Channel Michelson Interferometer 10. Since the length measuring apparatus does not constitute the instant invention, its basic operation not contained herein. The basic operation thereof is more specifically set forth in SAMSO Report TR-75-284 dated Dec. 10, 1975 entitled "Absolute Length Changes by Remote Interferometry," by E. G. Wolff and S. A. Eselun and only a brief analysis thereof is set forth hereinbelow.

Figure 2:
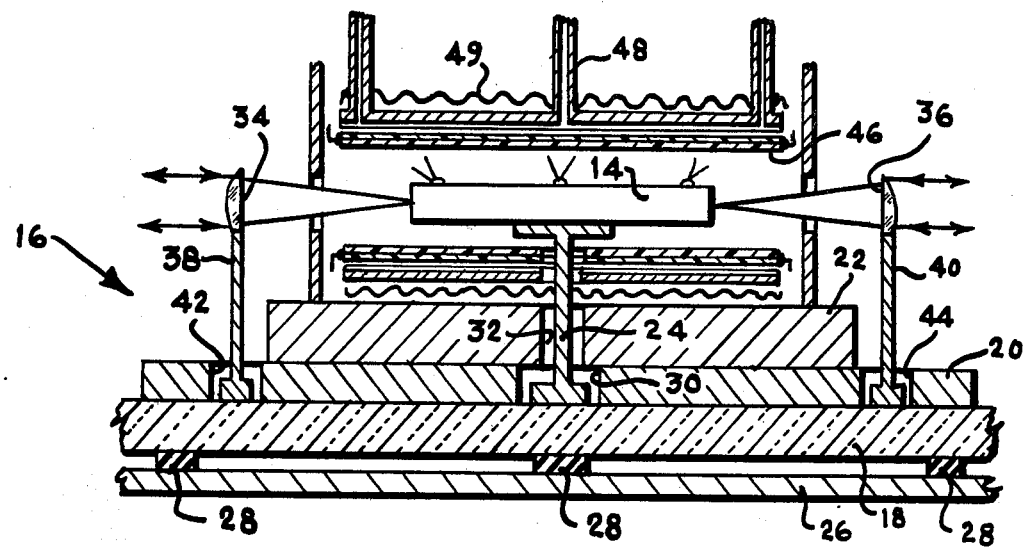
FIG. 2 is a schematic illustration, shown partly in cross-section, of the test sample support assembly of this invention.
Figure 3:
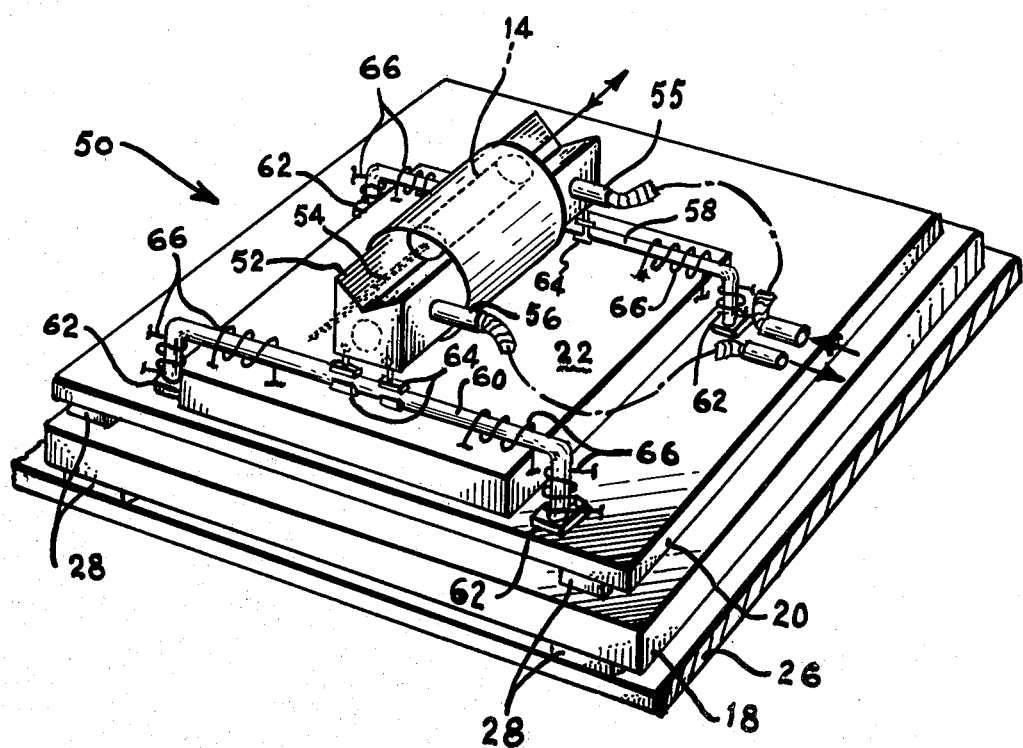
FIG. 3 is a pictorial representation of a further embodiment of the test sample support assembly of this invention.

Two Channel Michelson Interferometer 10 is primarily made up of a vacuum chamber 12 in which the test sample 14 is supported by the test sample support assembly 16 or test sample support assembly 50 clearly illustrated in FIGS. 2 and 3, respectively, of the drawing. Included within the Two Channel Michelson Interferometer are a radiant energy source (coherent light) such as laser 17, appropriate beam directing elements such as lenses $L_1$ and $L_2$ and corner mirror $M_1$, beamsplitters $B_3$, $B_2$ and $B_1$ as well as mirrors $M_2$, $M_3$, $M_4$, $M_5$ and $M_6$.

The principle of Two Channel Michelson Interferometer 10 is set forth with reference to FIG. 1 of the drawing. The original laser beam 19 (frequency-stabilized He-Ne) is split 50/50 at beam splitter $B_3$ into right and left (sample) side interferometers. The right and left sample ends are designated $S_1$ and $S_2$, respectively, and the mirrors M. For the right-hand side $S_1$ of sample, 14, the interferometer optical path length difference (OPLD) is $$OPLD_1 = \overline{B_1S_1} - \overline{B_1M_6}$$

Similarly $$OPLD_2 = \overline{B_2M_5} - \overline{S_2M_4} - \overline{B_2M_4}$$

Now $$\Delta OPLD_2 - \Delta OPLD_1 = \overline{\Delta B_2M_5} - \overline{\Delta S_2M_4} - \overline{\Delta B_2M_4} - \overline{\Delta B_1S_1} + \overline{\Delta B_1M_6}$$

Assume that $$\overline{\Delta B_2M_4} = \overline{\Delta B_1M_6}$$

$$\overline{\Delta B_1M_4} = \overline{\Delta B_2M_5}$$

Note that $$\overline{\Delta B_1M_4} = \overline{\Delta S_2M_4} + \Delta L_s + \overline{\Delta S_1B_1}$$

where $L_s$ is the sample length. Hence $$\Delta L_s = \Delta OPLD_2 - \Delta OPLD_1$$

Consequently, the sample length change $\Delta L_S$ is merely the difference between the changes in the optical path length differences.

Reference is now made to FIG. 2 of the drawing which shows in a schematic fashion, and partly in cross section the test sample support assembly 16 of this invention. Although not limited thereto, test sample support assembly 16 finds its greatest utility when incorporated within the Two Channel Michelson Interferometer 10 of type described with reference to FIG. 1 of the drawing. By proper support of test sample 14, the Two Channel Michelson Interferometer 10 is capable of measuring the length change of test sample 14.

Sample support assembly 16 is basically made up of a main support 18, a pair of insulating members 20 and 22 and a sample support 24, the detailed description of which is set forth hereinbelow. Since the optical elements making up Two Channel Michelson Interferometer 10 are mounted upon main support 18 it is essential that main support 18 be made of a suitable ultra-low expansion material. An example of such a material would be $SiO_2 + 7\% \ TiO_2$. Main support 18 is mounted in any conventional manner upon the base 26 of the vacuum chamber 12 of the Michelson Interferometer 10. For stability, mounts 28, preferably made of rubber, may be interposed between support 18 and base 26. It is again emphasized that main support 18 must have an extremely low expansion coefficient in order to maintain the stability of the optical equipment on support 18.

In order to further isolate main support 18 from the temperatures which are maintained within the test vacuum chamber 12, it is necessary to place upon support 18 a first insulating member 20. Insulating member 20 to be effective must be made of any suitable material of high thermal conductivity such as copper in order to substantially eliminate the temperature gradients in main support 18.

Situated upon first insulating member 20 is a second insulating member 22. Insulation 22, which is directly exposed to the vacuum of the test chamber, is made of any suitable material capable of providing insulation as well as being effective within a vacuum such as open porous silica brick. It is essential that this porous silica brick be open so as to be effective while situated within a vacuum.

The actual sample support 24 is secured directly to main support 18, protruding through openings 30 and 32 located centrally within insulating members 20 and 22, respectively. Sample support 24 is made of any suitable material which provides minimal distortion such as Invar and is preferably in the shape of an I-beam.

Even though assembly 16 of this invention is extremely effective in mounting sample 14, sample rotations of test sample 14 may take place during the measuring procedure. Therefore, focusing lenses 34 and 36 situated at opposite ends of sample 14 and mounted upon supports 38 and 40, respectively, are generally required. Supports 38 and 40 are fixedly secured to main support 18 along with the other optics of Interferometer 10. A pair of openings 42 and 44 are located within insulating member 20 in order to allow supports 38 and 40, respectively, to pass therethrough.

Test support assembly 16 is effective within a radiation type heat transfer method. In such an operation the surrounding environment of test sample 14 is either heated by means of a heater 46 in the form of, for example, a Nichrome wire heater in a Mullite insulator or cooled by the means of any suitable coolant such as liquid nitrogen which is fed through a tube-like arrangement 48 surrounding test sample 14. In addition, in order to maintain test sample 14 at its preselected temperature, a cylindrical insulating sheath 49 (more clearly illustrated in FIG. 3 of the drawing) made of any suitable insulation material such as aluminum/mylar encompasses test sample 14.

As a result of the test sample support assembly 16 of this invention, movement of the optical equipment situated on main support 18 is virtually eliminated so as to allow proper measurements of the thermal strain of test sample 14 to be taken.

Unfortunately, within a radiation heat transfer arrangement of the type set forth hereinabove and clearly depicted in FIG. 2 of the drawing, cooling of test sample 14 is a much more difficult procedure than heating. Consequently, for proper cooling of test sample 14 to take place, it is preferable that a conduction method be utilized. Such an arrangement is more clearly illustrated in FIG. 3 of the drawing. Therefore, in order to compensate for variations in the optical path length of the optics involved in Two Channel Michelson Interferometer 10, utilized in a conduction arrangement, this invention sets forth a modified test sample support assembly 50 clearly illustrated in pictorial fashion in FIG. 3.

Since some of the elements making up test sample support assembly 50 will be substantially identical to those elements making up support assembly 16 and as shown in FIG. 2 of the drawing, identical numerals will be utilized for identical elements. In this manner a more clear interrelationship between sample support assemblies 16 and 50 can be made. As with test sample support assembly 16, sample support assembly 50 is made up of main support 18 and a pair of insulating members 20 and 22. Main support 18 is mounted upon the base 26 of vacuum chamber 12 of Michelson Interferometer 10 with rubber mounts 28 interposed therebetween. The main support 18 is made of any suitable ultra-low expansion material such as $SiO_2 + 7\%$ $TiO_2$.

Mounted upon main support 18 is insulating element 20 made of any high, thermal conductive material, such as copper. Insulating member 20 is capable of substantially eliminating the temperature gradients within support 18. Additionally, situated upon insulating element 20 is insulating member 22 made of any suitable material such as open porous silica brick.

With the test sample support assembly 50 of this invention, shown in FIG. 3 of the drawing, since conduction is the method of cooling (or heating) test sample 14, it is necessary to mount sample 14 directly upon the sample support 52. For proper conduction to take place sample support 52 is made of a high thermal conductive material such as copper having a V-shaped groove 54 in the top portion thereof to support sample 14. The interior of support 52 is hollow so as to accept inlet and outlet pipes 55 and 56, respectively, which enables any suitable coolant such as liquid nitrogen to be pumped therethrough in order to cool support 52 and therefore sample 14.

The test sample support 52 is mounted upon a pair of steel support rods 58 and 60 which are affixed at opposite ends thereof to insulating member 20. Interposed between the ends of rods 58 and 60 insulating member 20 are mounting blocks 62 made of any suitable non-deformable material such as Invar. Test sample support 52 is clamped to the center of steel support rods 58 and 60 by any suitable securing means such as clamps 64.

Since some displacement of the sample support 52 will take place, it is necessary to compensate for this movement by any suitable mechanism capable of moving test support 52 in a plurality of directions. In test sample support assembly 50 of this invention, this is accomplished by means of a plurality of resistance heaters 66 located at a plurality of positions along steel support rods 58 and 60, respectively, by the appropriate application of voltage from any suitable source (not shown) thereacross. The application or non-application of this voltage causes the subsequent heating or cooling, respectively, of steel support rods 58 and 60 such that it expands (or contracts) by an appropriate amount in order to create minimal movement of support 52. This movement is sufficient to compensate any undesirable movement of support 51.

By use of support assembly 50 shown in FIG. 3 of the drawing, it is possible to eliminate not only the movement of the optical equipment located upon the main support 18, but also to compensate for any movement which may take place in test sample support 52.

Although this invention has been described with reference to particular embodiments, it will be understood to those skilled in the art that this invention is also capable of further and other embodiments within the spirit and scope of the appended claims.

We claim:

1. In a contactless length measuring device having a chamber for housing optical equipment for performing the length measurement operation of a sample and means for providing a preselected temperature within said chamber, the improvement therein being in the form of a support assembly located within said chamber for holding said sample in optical alignment with said optical equipment, said sample support assembly comprising a main support on which said optical equipment is mounted, said main support being made of a material having ultra-low expansion properties, a first insulating member juxtaposed said main support, said first insulating member being made of a material having relatively high thermal conductivity thereby substantially eliminating temperature gradients in said main support, a second insulating member juxtaposed said first insulating member, said second insulating member being made of an open porous material, means made of a thermally conductive material juxtaposed said second insulating member for supporting said sample in optical alignment with said optical equipment, said means for providing said preselected temperature being directly connected to said sample support means, and means interposed between said first insulating member and said sample support means for adjustably mounting said sample support means thereon whereby said main support and said optical equipment are rendered substantially unaffected by said preselected temperature within said chamber.

2. In a contactless length measuring device as defined in claim 1 wherein said means for adjustably mounting said sample support means comprises a pair of thermally conductive rods, each of said rods being secured to opposite sides of said sample support means, respectively, and fixedly secured to said first insulating member and means operably attached to said rods for altering the size thereof, thereby providing for the controlled movement of said sample support means.

3. In a contactless length measuring device as defined in claim 2 wherein said means for altering the size of said rods comprise resistance heaters.

4. In a contactless length measuring device as defined in claim 2 wherein said sample support means is hollow in the interior thereof and said means for providing said preselected temperature is operably connected to said interior of said sample support means thereby changing the temperature thereof.

5. A support assembly for holding a sample in an environment of preselected temperature comprising a main support, said main support being made of a material having ultra-low expansion properties, a first insulating member juxtaposed said main support, said first insulating member being made of a material having a relatively high thermal conductivity thereby substantially eliminating temperature gradients in said main support, a second insulating member juxtaposed said first insulating member, said second insulating member being made of an open porous material, means made of a thermally conductive material juxtaposed said second insulating member for supporting said sample within said preselected temperature environment, means for providing said preselected temperature being directly connected to said sample support means, and means interposed between said first insulating member and said sample support means for adjustably mounting said sample support means thereon whereby said main support is rendered substantially unaffected by said preselected temperature.

6. A support assembly as defined in claim 5 wherein said means for adjustably mounting said sample support means comprises a pair of thermally conductive rods, each of said rods being to secured opposite sides of said sample support means, respectively, and fixedly secured to said first insulating member, and means operably attached to said rods for altering the size thereof thereby providing for the controlled movement of said sample support means.

7. A support assembly as defined in claim 6 wherein said sample support means is hollow in the interior thereof and said means for providing said preselected temperature is operably connected to said interior of said sample support means thereby changing the temperature thereof.

8. A support assembly as defined in claim 5 wherein said material of said first insulating member is copper and said material of said second insulating member is open porous silica brick.

* * * * *